(12) United States Patent
Sinha (10) Patent No.: US 9,795,412 B2
(45) Date of Patent: Oct. 24, 2017

(54) BONE COMPRESSION AND FIXATION DEVICES

(75) Inventor: Amit Sinha, Fort Washington, PA (US)

(73) Assignee: GENOSSIS LLC, Fort Washington, PA (US)

( * ) Notice: Subject to any disclaimer, the term of this patent is extended or adjusted under 35 U.S.C. 154(b) by 864 days.

(21) Appl. No.: 13/989,090

(22) PCT Filed: Nov. 29, 2011

(86) PCT No.: PCT/US2011/062370
§ 371 (c)(1),
(2), (4) Date: May 23, 2013

(87) PCT Pub. No.: WO2012/074991
PCT Pub. Date: Jun. 7, 2012

(65) Prior Publication Data
US 2013/0238036 A1    Sep. 12, 2013

Related U.S. Application Data (60) Provisional application No. 61/417,981, filed on Nov. 30, 2010, provisional application No. 61/417,985, filed on Nov. 30, 2010.

(51) Int. Cl.
*A61B 17/68* (2006.01)
*A61B 17/88* (2006.01)
(Continued)

(52) U.S. Cl.
CPC .......... *A61B 17/68* (2013.01); *A61B 17/7208* (2013.01); *A61B 17/863* (2013.01);
(Continued)

(58) Field of Classification Search
CPC ..... A61B 17/842; A61B 17/844; A61B 17/86; A61B 17/8625; A61B 17/863;
(Continued)

(56) References Cited

U.S. PATENT DOCUMENTS

| 4,456,005 A | 6/1984 | Lichty |
| 4,640,271 A * | 2/1987 | Lower ................. A61B 17/742 606/105 |

(Continued)

FOREIGN PATENT DOCUMENTS

| EP | 0325682 A1 | 8/1989 |
| EP | 2590576 A1 | 3/2014 |
| WO | 2004069031 A2 | 8/2004 |

OTHER PUBLICATIONS

International Search Report mailed Mar. 12, 2012 for International Application No. PCT/US2011/062370.
(Continued)

*Primary Examiner* — Kevin T Truong
*Assistant Examiner* — Tracy Kamikawa
(74) *Attorney, Agent, or Firm* — Morgan, Lewis & Bockius LLP (57) ABSTRACT

A bone screw, for drawing first and second bone fragments together, includes a shaft having a distal section and a proximal section. The distal section has a first external male screw thread and a minor diameter. The proximal section has a second external male screw thread. A major diameter of the distal section is larger than a major diameter of the proximal section. The bone screw includes a sleeve that has an internal female screw thread configured to mate with the second male screw thread. A distal portion of the sleeve has an outer diameter. The outer diameter is equal to or smaller than the minor diameter of the distal section of the shaft.

10 Claims, 9 Drawing Sheets

(51) Int. Cl.
  *A61B 17/72* (2006.01)
  *A61B 17/86* (2006.01)

(52) U.S. Cl.
  CPC .......... *A61B 17/8685* (2013.01); *A61B 17/88* (2013.01); *A61B 17/8888* (2013.01); *A61B 17/7241* (2013.01); *A61B 17/864* (2013.01); *A61B 17/8615* (2013.01); *A61B 17/8891* (2013.01); *A61B 2017/681* (2013.01)

(58) Field of Classification Search
  CPC ............ A61B 17/8635; A61B 17/8645; A61B 17/8665; A61B 17/8685; A61B 17/683; A61B 17/686; A61B 17/7225; A61B 2017/8655; A61B 2017/867; A61B 2017/8675; A61B 2017/868; A61B 2017/681; F16B 25/00; F16B 25/0036; F16B 25/0042; F16B 25/0057; F16B 25/0063; F16B 25/0068; F16B 25/0073; F16B 25/0084; F16B 25/0094
  See application file for complete search history.

(56) References Cited

U.S. PATENT DOCUMENTS

| | | | |
|---|---|---|---|
| 5,498,265 A | 3/1996 | Asnis et al. | |
| 5,743,912 A | 4/1998 | Lahille et al. | |
| 5,879,352 A | 3/1999 | Filoso et al. | |
| 5,989,255 A * | 11/1999 | Pepper | A61B 17/8685 606/306 |
| 5,997,538 A * | 12/1999 | Asnis | A61B 17/8625 606/301 |
| 6,511,481 B2 * | 1/2003 | von Hoffmann | A61B 17/68 606/60 |
| 6,951,561 B2 * | 10/2005 | Warren | A61B 17/68 606/328 |
| 7,517,350 B2 * | 4/2009 | Weiner | A61B 17/8605 606/105 |
| 7,582,107 B2 * | 9/2009 | Trail | A61B 17/863 606/304 |
| 7,648,523 B2 * | 1/2010 | Mirkovic | A61B 17/1637 606/279 |
| 8,303,634 B2 | 11/2012 | Martin | |
| 2003/0149436 A1 * | 8/2003 | McDowell | A61B 17/68 606/916 |
| 2003/0187447 A1 | 10/2003 | Ferrante et al. | |
| 2009/0254129 A1 | 10/2009 | Tipirneni | |
| 2010/0057214 A1 | 3/2010 | Graham et al. | |

OTHER PUBLICATIONS

Written Opinion mailed Mar. 12, 2012 for International Application No. PCT/US2011/062370.
Examination Report dated Mar. 3, 2015 for European Patent Application No. 11 844 192.2.
Supplementary European Search Report mailed Apr. 14, 2014 for European Patent Application No. 1184192.2.

* cited by examiner

BONE COMPRESSION AND FIXATION DEVICES

CROSS-REFERENCE TO RELATED APPLICATIONS

This application is a U.S. national stage of International Patent Application PCT/US2011/062370 filed Nov. 29, 2011 entitled "Bone Compression and Fixation Devices, which claims the benefit of U.S. Provisional Patent Application No. 61/417,985 filed Nov. 30, 2010 entitled "Compression Screw" and U.S. Provisional Patent Application No. 61/417,981 filed Nov. 30, 2010 entitled "Flexible to Rigid Bone Fixation Device", all of which are incorporated by reference herein in their entirety. U.S. Provisional Patent Application No. 61/415,953 filed Nov. 22, 2010 entitled "Compression Wire" is also incorporated by reference in its entirety.

BACKGROUND OF THE INVENTION

The present invention generally relates to bone compression and fixation devices and in some particular embodiments, orthopedic devices for joining together in compression two or more pieces of a fractured bone for optimum healing.

BRIEF SUMMARY OF THE INVENTION

In one embodiment there is a bone screw for drawing first and second bone fragments together comprising a shaft having a distal section and a proximal section, the distal section having a first external male screw thread and a minor diameter, the proximal section having a second external male screw thread, a major diameter of the distal section being larger than a major diameter of the proximal section; and a sleeve having an internal female screw thread configured to mate with the second male screw thread, a distal portion of the sleeve having an outer diameter, the outer diameter being equal to or smaller than the minor diameter of the distal section of the shaft.

In one embodiment, the sleeve is configured to receive a tool to rotate the shaft and sleeve together when the shaft is driven into a first bone fragment or rotate the sleeve relative to the shaft to draw a second bone fragment toward the first bone fragment. In one embodiment, a pitch of the first external male screw thread is larger than a pitch of the second external male screw thread. In one embodiment, the distal portion of the sleeve is tapered. In one embodiment, the sleeve includes two or more external longitudinally extending slots configured to engage a tool.

In one embodiment, the distal portion of the sleeve is smooth. In one embodiment, the shaft is cannulated. In one embodiment, the shaft includes at least one aperture along a length of the shaft in fluid communication with a hollow center of the shaft. In one embodiment, the shaft includes a plurality of apertures along a length of the shaft, the plurality of apertures being in fluid communication with one another.

In another embodiment, there is a bone screw system for drawing first and second bone fragments together, comprising: a bone screw including: a shaft having a distal section and a proximal section, the distal section having a first external male screw thread, the proximal section having a second external male screw thread, a major diameter of the distal section being larger than a major diameter of the proximal section; and a sleeve having an internal female screw thread engageable with the second male screw thread, the sleeve being configured to receive a first tool for rotating the shaft and sleeve together and a second tool for rotating the sleeve relative to the shaft; a tool including: a first tool portion configured to rotate the sleeve relative to the shaft; and a second tool portion configured to rotate the shaft and the sleeve together.

In one embodiment, the second tool portion includes a threaded distal end that is engageable with the internal female screw thread and abuts the proximal section. In one embodiment, the second tool portion extends through the first tool portion when rotating the shaft and sleeve together and the second tool portion is withdrawn from the first tool portion when rotating the sleeve relative to the shaft.

In another embodiment, there is a wire device for drawing first and second bone fragments together, comprising: a wire having an external male thread; and a sleeve having an internal female thread configured to mate with the external male thread. In one embodiment, the sleeve is configured to slide over the external male thread in a distal direction without rotating the sleeve relative to the wire. In one embodiment, the sleeve includes two or more axially extending slots to form two or more phalanges. In one embodiment, the wire includes a distal section and a proximal section, the distal section having a first external male screw thread, the proximal section having a second external male screw thread, a major diameter of the distal section being larger than a major diameter of the proximal section.

In one embodiment, a pitch of the first external male screw thread is larger than a pitch of the second external male crew thread. In one embodiment, the sleeve includes two or more radially extending projections. In one embodiment, a distal portion of the sleeve has a diameter equal to or smaller than a minor diameter of the wire. In one embodiment, the sleeve is tapered.

In another embodiment there is a method for drawing first and second bone fragments together, comprising: screwing a wire having an external male thread into a first bone fragment; sliding a sleeve having an internal female thread configured to mate with the external male thread along the wire without rotating the sleeve relative to the wire to abut a second bone fragment; rotating the sleeve relative to the wire to draw the second bone fragment toward the first bone fragment, a proximal portion of the wire extending proximally from the second bone fragment and the sleeve; and cutting and removing the proximal portion of the wire from the remainder of the wire.

In another embodiment there is a bone fixation device comprising: a distal end configured to attached to a first bone section and a proximal end configured to attached to a second bone section, a flexible body secured to the distal end and movably attached to the proximal end; and a plurality of cannulated rigid segments surrounding the body, wherein the segments are spaced and allow the body to flex when the body is in a first position relative to the proximal end and wherein the segments abut and prevent the body from being flexed when the plate is moved from the first position to a second position relative to the proximal end.

In one embodiment, the body is flexible along a first plane and rigid along a second plane, the first plane being orthogonal to the second plane. In one embodiment, the body has a rectangular cross section. In one embodiment, the body is threadably attached to a radially rotatable, axially fixed sleeve in the proximal end. In one embodiment, each segment includes a projection that mates with an indent of an adjacent segment in the second position. In one embodiment, the segments are cylindrically shaped. In one embodiment, the body includes at least one aperture and the proximal end includes at least one aperture, the at least one aperture of the body aligning with the at least one aperture of the proximal end in the second position.

BRIEF DESCRIPTION OF THE SEVERAL VIEWS OF THE DRAWINGS

The foregoing summary, as well as the following detailed description of embodiments of the bone compression and fixation devices, will be better understood when read in conjunction with the appended drawings of exemplary embodiments. It should be understood, however, that the invention is not limited to the precise arrangements and instrumentalities shown.

In the drawings.

DETAILED DESCRIPTION OF THE INVENTION

In orthopedic surgery it is common to rejoin broken bones. However, in most situations where cross-fixation of the bone fragments is required, the success of the surgical procedure depends to a large extent on the degree of compression that can be achieved between the bone fragments. More specifically, if the surgeon is unable to bring the bone fragments in close contact with each other, there will exist a space or void into which the bone tissue must grow before the healing process is complete. Thus, the greater the distance between the bone fragments, the slower the healing process. In addition, the healing process can be retarded by any relative movement or shifting of the bone fragments which disturbs the bone tissue that has been laid down.

Screws commonly used in fracture fixation are of the lag type, and comprise a threaded leading end and an enlarged head incorporating a means to engage a driving tool at the trailing end. In some situations, the presence of a screw head has a deleterious effect on the outcome of the repair, specifically in cases where the screw must be inserted in or near a skeletal joint or where inadequate bone stock is available to allow countersinking of the screw head.

Typical headless compression screws, such as the Hubert Screw which achieves compression by providing two different thread pitches, one pitch toward a distal end an a different pitch toward a proximal end. Apart from being technique sensitive, the ability to compress the bone segments together with a Hubert Screw is based on the number of threads in the head. This allows for limited amount of compression. In some situation, a screw head is desirable but the head contacts the outer surface of the bone at the wrong time to provide the desired compression.

In some exemplary embodiments of the present invention, a screw device 10 includes a two piece construction that allows for improved compression between bone fragments. Though screw device 10 may be used with any bone fragments, in some embodiments, screw device 10 is configured for use with the small bones of the hand or foot. Any dimensions specifically mentioned below may be varied in some embodiments to accommodate a particular anatomy.

Figures 1A, 1B:
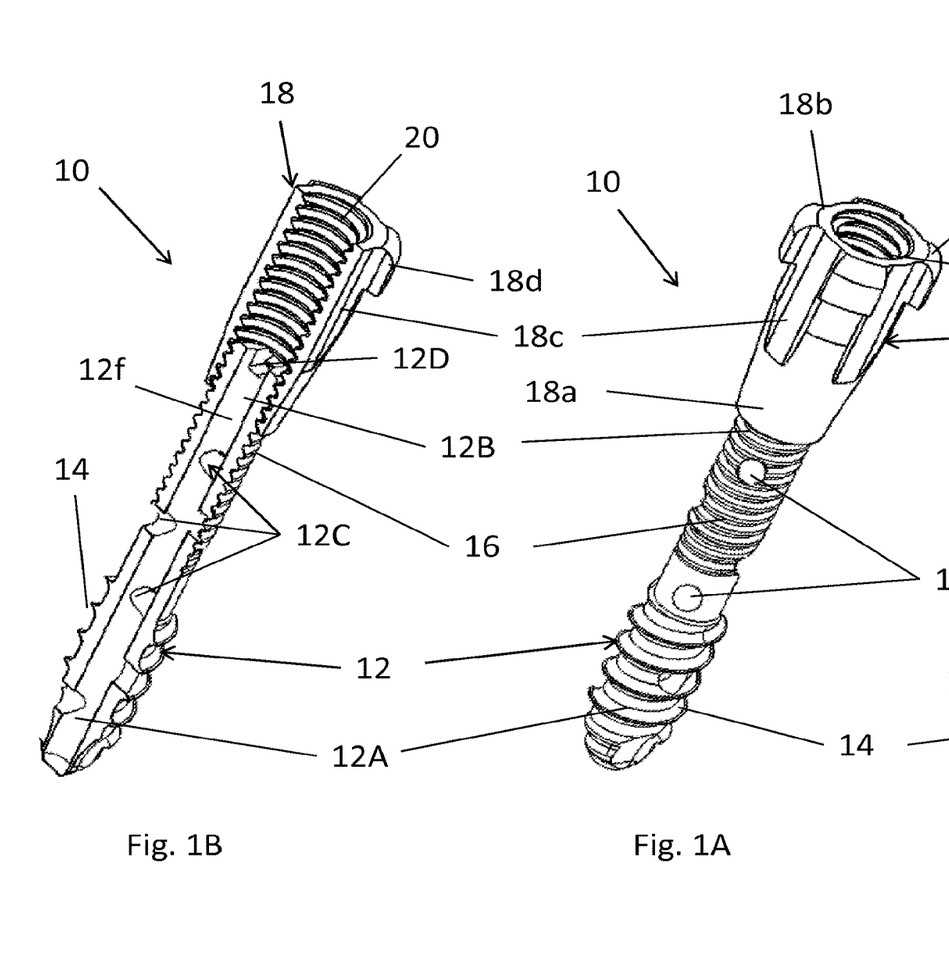
FIG. 1A is a perspective view of a bone screw device in accordance with an exemplary embodiment of the present invention.
FIG. 1B is cross sectional perspective view of the bone screw device shown in FIG. 1A.
Figure 1C:
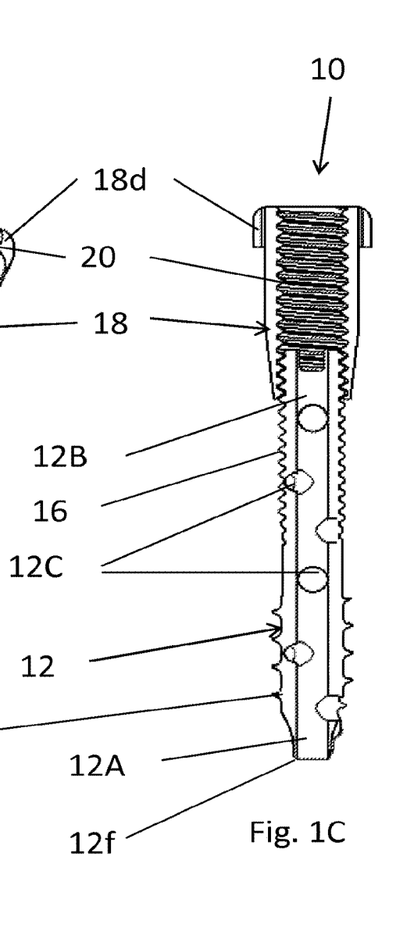
FIG. 1C is cross sectional side view of the bone screw device shown in FIG. 1A.
Figure 2A:
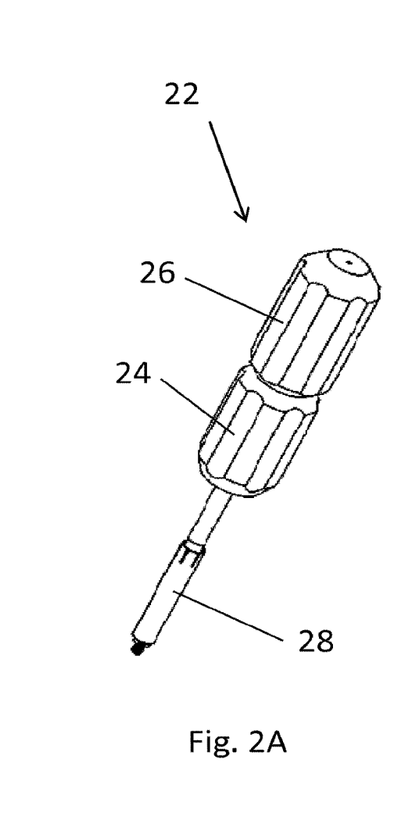
FIG. 2A is a perspective view of a tool for implanting a bone screw device in accordance with an exemplary embodiment of the present invention.
Figure 2B:
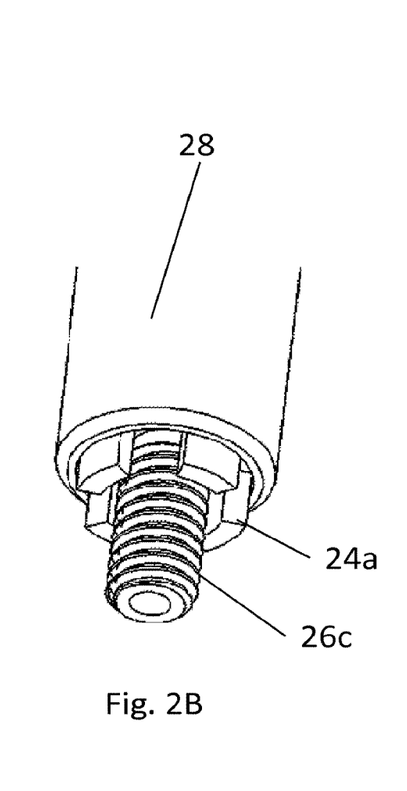
FIG. 2B is a perspective view of the tool shown in FIG. 2A.
Figure 2C:
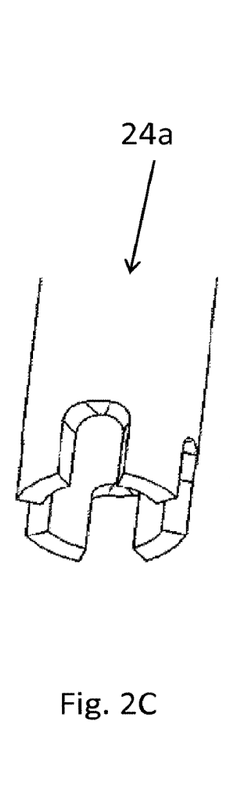
FIG. 2C is a perspective view of a distal end of a sleeve of the tool shown in FIG. 2A.
Figure 2D:
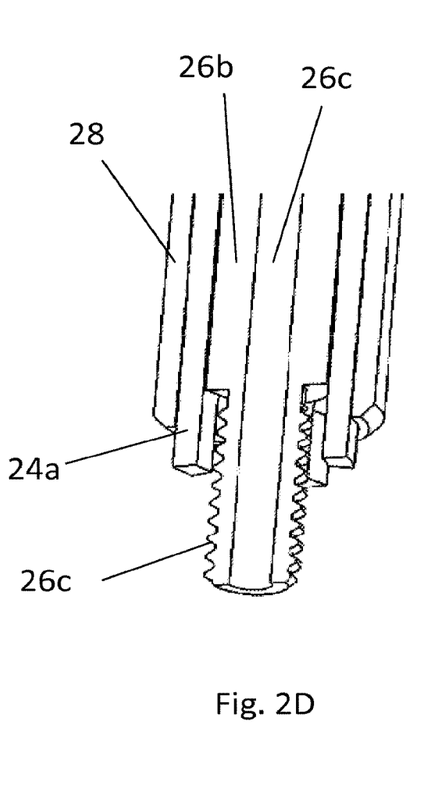
FIG. 2D is a cross sectional perspective view of the tool shown in FIG. 2A.

Referring to FIGS. 1A-1C, screw device 10 includes a shaft 12 and a sleeve 18 that is movable along the shaft 12 to draw together at least two bone fragments.

In one embodiment, shaft 12 has a distal section 12a and a proximal section 12b. In one embodiment, the distal end of distal section 12a is pointed. In other embodiments, the distal end of distal section 12a is generally blunt. In one embodiment, a major diameter of distal section 12a is larger than a major diameter of proximal section 12b. In other embodiments, the major diameters of distal section 12a and proximal section 12b are equal. In one embodiment, the major diameter of distal section 12a and proximal section 12b are approximately 2.5 mm to approximately 10 mm. In one embodiment, the length of screw device 10 is approximately 10 mm-approximately 60 mm.

In one embodiment, distal section 12a includes a first external male screw thread 14. In one embodiment, proximal section 12b includes a second external male screw thread 16. In one embodiment, first external male screw thread 14 is configured to engage cortical and/or cancellous bone. In one embodiment, second external male screw thread 16 are machine threads configured to mate with sleeve 18 and allow the sleeve to travel down the length of shaft 12 as discussed below. In one embodiment, a pitch of first external male screw thread 14 is larger than a pitch of the second external male screw thread 16. In one embodiment, the pitch of first external male screw thread 14 is approximately 1 mm and the pitch of second external male screw thread 16 is approximately 0.45 mm. In other embodiments, the pitch of first external male screw thread 14 is equal to the pitch of second external male screw thread 16.

In one embodiment, shaft 12 is cannulated. In one embodiment, the entire shaft 12 is cannulated (bore 12f) such that both ends of shaft 12 are open and in fluid communication with one another. In one embodiment, shaft 12 is cannulated axially to allow screw device 10 to be driven over a guide wire. In one embodiment, the diameter of bore 12f is approximately 2.6 mm. In one embodiment, the diameter of bore 12f is approximately 1 mm or larger. In other embodiments, only a portion of shaft 12 is cannulated and/or one or more of the ends are closed. In one embodiment, shaft 12 includes at least one aperture 12c along a length of shaft 12 and in fluid communication with a hollow center of shaft 12. In one embodiment, shaft 12 includes a plurality of apertures 12c along a length of shaft 12, apertures 12c are in fluid communication with one another. In one embodiment, apertures 12c align with a corresponding diametrically opposed aperture 12c. In one embodiment, apertures 12c have a corresponding opposed aperture 12c on the opposite site of shaft 12 that is at an angle relative to the longitudinal axis of shaft 12. In other embodiments, apertures 12c do not have a corresponding aperture 12c on the opposite side of shaft 12. In one embodiment, apertures 12c are approximately 0.2 mm in diameter. In other embodiments, apertures 12c are larger than 0.2 mm in diameter. In one embodiment, apertures 12c are circular. In other embodiments, apertures 12c are any shape including triangular, rectangular or oval.

In one embodiment, apertures 12c and/or cannulated shaft 12 allow for fluid such as blood to vascularize the fracture site and aid in fracture healing. In one embodiment, apertures 12c and/or cannulated shaft 12 allow for fluid to exit the body while implanting screw device 10 rather than cause a buildup of pressure within the body. In other embodiments, apertures 12c and cannulated shaft 12 may be used to deliver a drug such as gentamicin or a bone graft through or from within screw 12 to the fracture site.

In one embodiment, the proximal end of shaft 12 includes a keyed surface 12d. In one embodiment, keyed surface 12d is a slot. In one embodiment, keyed surface 12d is configured to engage a driver tool to provide counter torque or to drive shaft 12 directly if necessary.

In one embodiment, sleeve 18 threadably mates with proximal section 12b of shaft 12. In one embodiment, sleeve 18 includes an internal female screw thread 20 that is configured to mate with second external male screw thread 16. In one embodiment, the length of sleeve 18 is approximately 7 mm.

In one embodiment, sleeve 18 is tapered toward distal section 12a. In one embodiment at least a portion of sleeve 18 is frustoconical in shape. In one embodiment, an outer surface of at least a distal portion of sleeve 18 is smooth. In one embodiment, the outer surface of at least a distal portion of sleeve 18 is void of threads. In one embodiment, the outer diameter of at least a portion of the distal portion of sleeve 18 is approximately equal to or smaller than the minor diameter of distal section 12a of shaft 12. In one embodiment, the diameter of sleeve 18 is greater than the minor diameter of distal section 12a of shaft 12 and tapers toward distal end 18a to a diameter less than the minor diameter of distal section 12a of shaft 12. In one embodiment, providing a tapered sleeve 18 allows for a desired compression between bone fragments without having to screw sleeve 18 into the bone. In one embodiment, shaft 12 and sleeve 18 are configured to allow the distal end of sleeve 18 to abut against the beginning of first external male screw thread 14.

In one embodiment, sleeve 18 includes two or more external longitudinally extending slots 18c that are configured to engage a tool as discussed below. In other embodiments, sleeve 18 may include an internal hex, slot, projection, Torx or Phillips shape for receiving the tool. In one embodiment, sleeve 18 includes two or more radially extending projections 18d. In one embodiment, radially extending projections 18d act as a screw head to engage a bone surface. In other embodiments, sleeve 18 does not include radially extending projections 18d and is instead configured to be completely countersunk into the bone and generally flush with the outer bone surface. In one embodiment, projections 18d are countersunk into the bone. In one embodiment, sleeve 18 remains at the outer surface of the bone.

In one embodiment, screw device 10 is comprised of biocompatible materials. In one embodiment, screw device 10 is comprised of biocompatible metal, such as stainless steel or titanium. In one embodiment, screw device 10 is comprised of biocompatible polymer such as PEEK.

Referring to FIGS. 2A-2D, a tool 22 may be used to implant screw device 10. In one embodiment, tool 22 is an at least two piece design that has an outer drive sleeve 24a and an inner drive shaft 26b. In one embodiment, tool 22 is a three piece design with outer drive sleeve 24a including a lock sleeve 28. In one embodiment, inner drive shaft 26b mates with internal female screw thread 20 of sleeve 18 while drive sleeve 24a engages slots 18d of sleeve 18.

In one embodiment, tool 22 includes a first tool portion 24 and a second tool portion 26. In one embodiment, first tool portion 24 is configured to rotate sleeve 18 relative to shaft 12. In one embodiment, second tool portion 26 is configured to rotate the shaft and sleeve together.

Figure 3A:
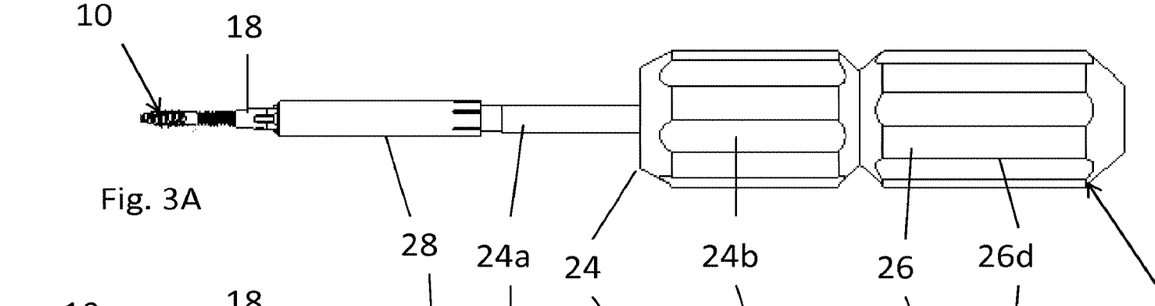
FIG. 3A is a side elevational view of the bone screw device shown in FIG. 1A with a tool in accordance with an exemplary embodiment of the present invention.
Figures 3B, 3C:
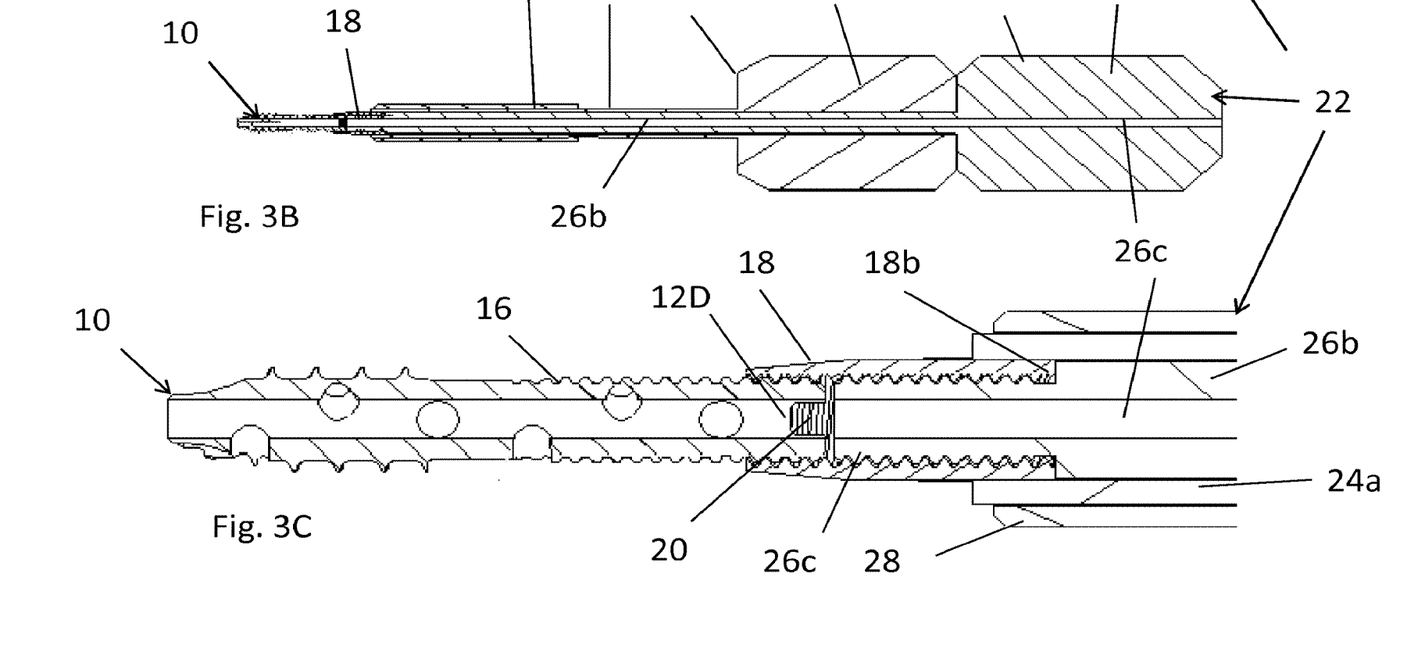
FIG. 3B is a cross sectional view of the bone screw device and tool shown in FIG. 3A.
FIG. 3C is an enlarged cross section view of the bone screw device and tool shown in FIG. 3B.

Referring to FIGS. 3A-3C, in one embodiment, first tool portion 22 includes an enlarged handle 24b. In one embodiment, handle 24 is configured to be griped by a user's hand to torque first tool portion 24. In one embodiment, driver sleeve 24a extends axially from handle 24b. In one embodiment, second tool portion 22 includes an enlarged handle 26d. In one embodiment, drive shaft 26b extends axially from handle 26d. In one embodiment, handle 26d abuts handle 24b when drive shaft 26b extends through drive sleeve 24a. In one embodiment, handle 26d is releasably coupled to handle 24b to prevent drive shaft 26b from rotating relative to drive sleeve 24a during use. In one embodiment, second tool portion 26 includes an open bore 26c. In one embodiment, the diameter of bore 26c is equal to the diameter of bore 12f. In one embodiment, bore 26c allows for a guide wire extending from screw device 10 to extend through tool 22.

In one embodiment, drive sleeve 24a includes two or more axially extending projections corresponding to slots 18d of sleeve 18. In one embodiment, the axially extending projections are circumferentially spaced from one another such that this is an open space between each projection to form phalanges. In other embodiments, the projections of the drive sleeve 24a do not have an open space in between but instead project radially inward from the surrounding drive sleeve 24a. In one embodiment, drive shaft includes an external male screw thread 12c. In other embodiments, drive shaft 26b includes a mating surface other than a screw thread such as a hex, star, or Phillips. In one embodiment, the distal end of drive shaft 26b extends axially further than the distal end of drive sleeve 24a in a first position and the distal end of drive sleeve 24a extends axially further than the distal end of drive shaft 26b in a second position.

Figures 4A, 4B:
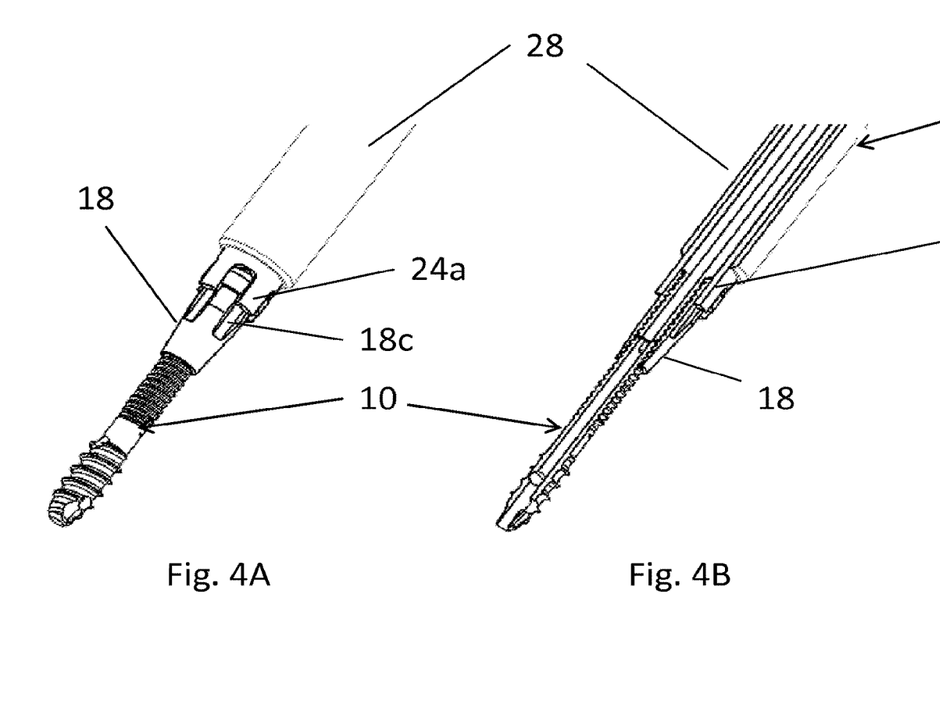
FIG. 4A is a perspective view of the bone screw device and tool shown in FIG. 2A in an initially engaged position.
FIG. 4B is a cross sectional perspective view of the bone screw device and tool shown in FIG. 4A.
Figure 4C:
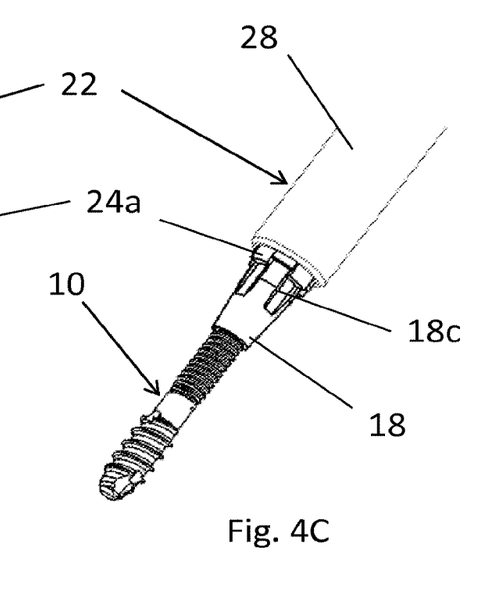
FIG. 4C is a perspective view of the bone screw device and tool shown in FIG. 4A in a fully engaged position with lock sleeve over the driver phalanges.

Referring to FIGS. 4A-4C, in one embodiment, a lock sleeve 28 is provided on the outer surface of drive sleeve 24a. In one embodiment, lock sleeve 28 is used to ensure that the distal phalanges of drive sleeve 24a do not flex radially and out of engagement with sleeve 18. In one embodiment, once drive shaft 26b and drive sleeve 24a are coupled to sleeve 18 in an initially engaged position (FIG. 4A), lock sleeve 28 is at least partially slid over distal phalanges of drive sleeve 24a in a fully engaged position (FIG. 4C).

Referring to FIGS. 3A-4C, in an exemplary method of use of screw device 10, shaft 12 and sleeve 18 are inserted into the fractured bone together using tool 22 coupled to sleeve 18. In one embodiment, the distal tip of shaft 12 engages and is screwed into the distal fragment of the fractured bone. In one embodiment, both first tool portion 24 and second tool portion 26 are rotated together such that shaft 12 is rotated without advancing sleeve 18 relative to shaft 12. In one embodiment, once the shaft 12 is in place, second tool portion 26 is unscrewed from sleeve 18 and at least partially withdrawn from first tool portion 24. First tool portion 24 including drive sleeve 24a then rotates sleeve 18 relative to shaft 12 advancing sleeve 18 distally axially along shaft 12. The outer surface of sleeve 18 contacts a proximal bone fragment and as sleeve 18 is advanced along shaft 12, screw device 10 draws the distal and proximal bone fragments together.

In one embodiment, sleeve 18 enters the proximal bone fragment and at least partially countersinks itself. In one embodiment, sleeve 18 is completely countersunk such that the proximal end of sleeve 18 is flush to the outer surface of the proximal bone fragment. In one embodiment, first tool portion 24 includes a torque gauge or a safety feature to prevent over compression of the bone fragments. In one embodiment, the excess portion of shaft 12, extending proximally from sleeve 18 after screw device 10 has been compressed, is cut or broken off from the remainder of shaft 12. In one embodiment, shaft 12 includes one or more points of weakness such as a score line or divot to aid in breaking off the excess portion of shaft 12. In one embodiment, the proximal end of shaft 12 is generally flush with the proximal end 18b of sleeve 18 after removing the excess portion of shaft 12.

In procedures requiring a smaller diameter implant or other procedures, a wire rather than a screw may be preferred. Typically Kirschner wires or K-wires are used to keep bone fragments in place in certain instances. However, K-wires have a single diameter and do not allow for effective compression.

Figure 5A:
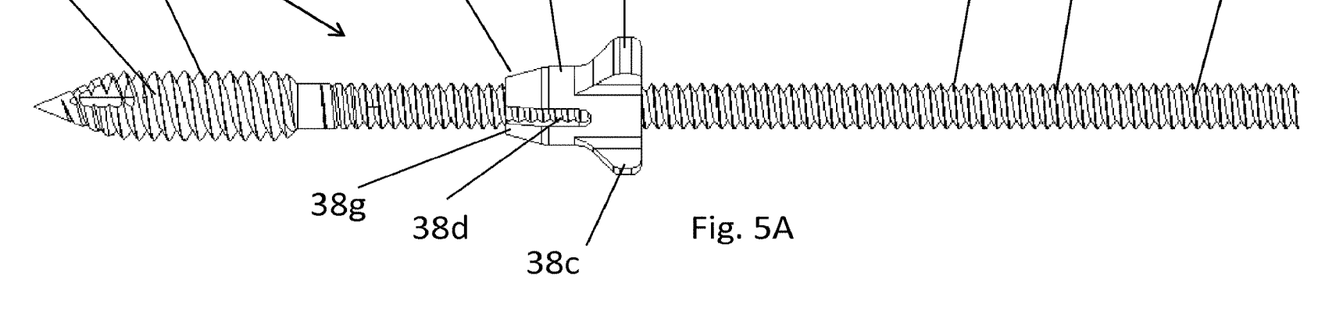
FIG. 5A is a side elevational view of a bone wire device in accordance with an exemplary embodiment of the present invention.
Figure 5B:
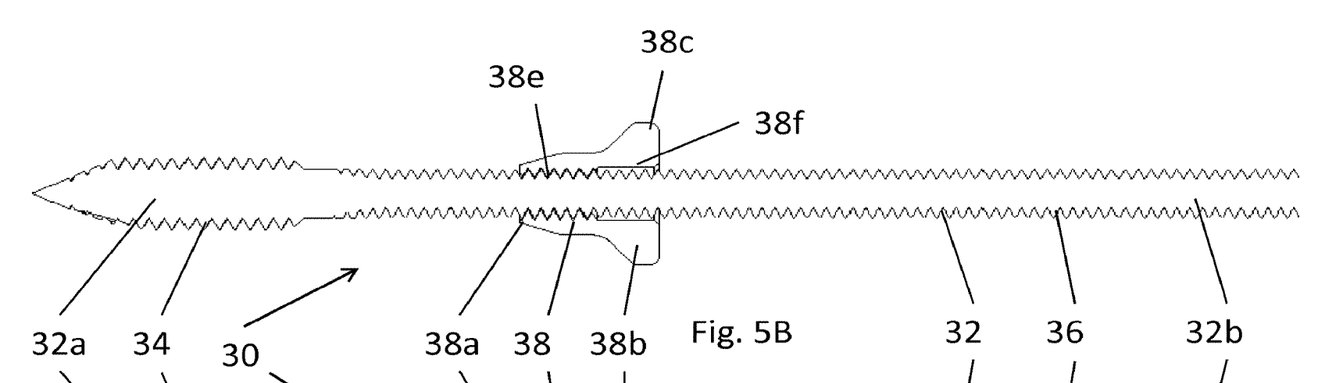
FIG. 5B is an outline of a cross sectional view of the bone wire device shown in FIG. 5A.

Referring to FIGS. 5A-5B, a wire device 30 includes a threaded wire 32 and a sleeve 38. In one embodiment, a distal tip of wire 32 engages the bone shaft and sleeve 38 is secured to wire 32 to compress one or more bone fragments together. The remaining wire may then be cut or broken off.

In one embodiment, a distal section 32a of wire 32 includes an external male screw thread 34. In one embodiment, the major diameter of wire 32 is approximately 1.3 mm. In one embodiment, external male screw thread 34 is a double lead pitch. In one embodiment, a proximal section 32b of wire 32 includes an external male screw thread 36. In one embodiment, the major diameter of distal section 32a is larger than the major diameter of proximal section 32b. In other embodiments, the major diameters of the distal section 32a and proximal section 32b are equal. In one embodiment, the pitch of external male screw thread 34 is larger than the pitch of external male screw thread 36. In other embodiments, the pitches of the external male screw threads 34, 36 are equal. In some embodiments, wire 32 includes a plurality of ribs in addition to or in place of external male screw thread 36. In one embodiment, the distal end of wire 32 is pointed. In other embodiments, distal end of wire 32 is blunt.

In one embodiment, sleeve 38 includes an internal female screw thread 38e configured to mate with the external male screw thread 36. In one embodiment, sleeve 38 is configured to slide over the external male screw thread 36 in a distal direction without rotating sleeve 38 relative to wire 32 but not slide in the proximal direction similar to a zip or cable tie. In one embodiment, sleeve 38 includes two or more axially extending slots 38d to form two or more flexible phalanges 38g. In one embodiment, internal female screw thread 38e is only on the flexible portion of sleeve 38. In one embodiment, a proximal section 38f of sleeve 38 is smooth and does not contain threads. In one embodiment, a distal portion of sleeve 38 has a diameter equal to or small than the major diameter of distal section 32. In one embodiment, distal end 38a of sleeve 38 is tapered. In one embodiment, the outer diameter of at least a portion of the distal portion of sleeve 38 is approximately equal to or smaller than the minor diameter of distal section 32a of wire 32. In one embodiment, the tapered section of sleeve 38 is greater than the minor diameter of distal section 32a of wire 32 and tapers toward distal end to a diameter less than the minor diameter of distal section 32a of wire 32. In one embodiment, wire 32 and sleeve 38 are configured to allow the distal end of sleeve 38 to abut against the beginning of external male screw thread 34.

In one embodiment, sleeve 38 includes two or more radially extending projections 38c. In one embodiment, projections 38c are toward the proximal end 38b of sleeve 38. In one embodiment, projections 38c allow for a tool or hand to more easily grasp and rotate sleeve 38 relative to wire 32. In one embodiment projection 38c act as a screw head and remain on the outer surface of the bone.

Figure 6A:
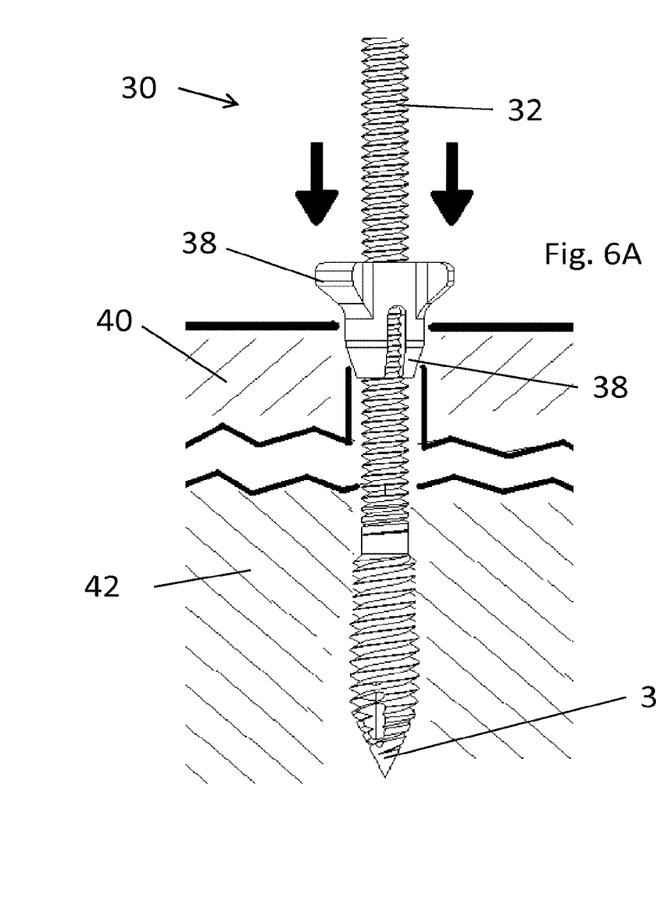
FIG. 6A is a side elevational view of the bone wire device shown in FIG. 5A between first and second bone fragments in an engaged position.
Figure 6B:
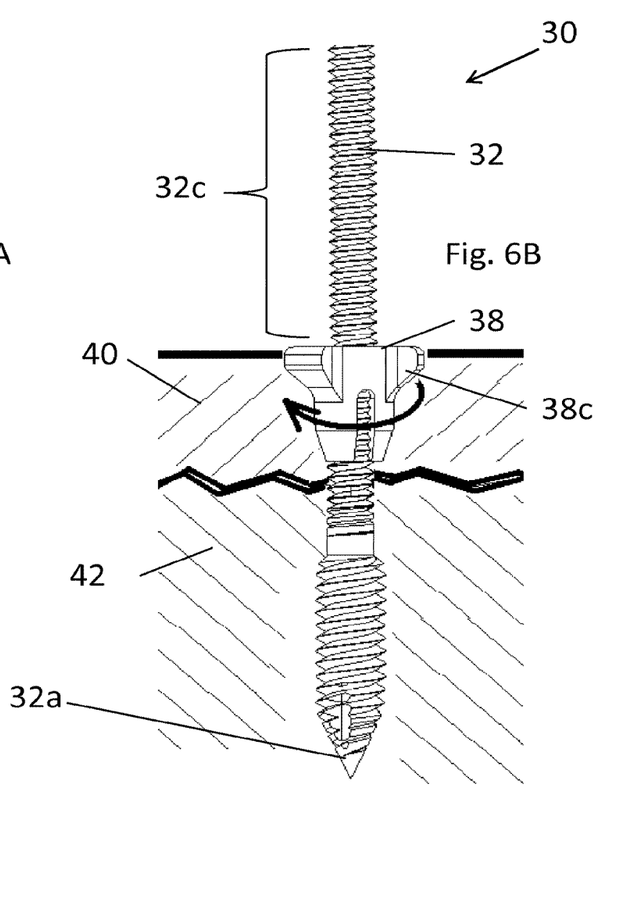
FIG. 6B is a side elevational view of the bone wire device shown in FIG. 6A in a compressed position.

Referring to FIGS. 6A and 6B, in an exemplary method of use, wire device 30 is inserted between at least a proximal bone fragment 40 and a distal bone fragment 42. In one embodiment, wire 32 is inserted using a wire driver. In one embodiment, wire 32 is screwed into distal bone fragment 42. In one embodiment, sleeve 38 is slid along wire 32 without rotating sleeve 38 relative to wire 32 until sleeve 38 abuts the outer surface of proximal bone fragment 40. In other embodiments, sleeve 38 is screwed to advance sleeve 38 along wire 32. In embodiments where proximal section 32b of wire 32 includes threads, once sleeve 38 abuts bone, sleeve 38 is rotated relative to wire 32 to draw distal bone fragment 42 and proximal bone fragment 40 together. In one embodiment, sleeve 38 is countersunk into proximal bone fragment 40. In other embodiments, projections 38c acts as a screw head to prevent sleeve 38 from completely countersinking. In one embodiment, once sleeve 38 is move to the desired position along wire 32, the remaining wire 32c proximate to sleeve 38 is cut or bent off from the remainder of wire 32.

In one embodiment, wire device 30 is comprised of biocompatible materials. In one embodiment, wire device 30 is comprised of biocompatible metal such as stainless steel or titanium. In one embodiment, wire device 30 is comprised of biocompatible polymer such as PEEK.

In certain bone fractures there is a need for a rod that will be flexible on insertion but can be converted to a rigid implant.

Referring to FIGS. 7-9B, a bone fixation device 50 is initially flexible and can be stiffened after implanting into the body. Bone fixation device 50 may be sized and configured to secure any two bones or bone fragments together including long bones having an intramedullary canal such as the humerus, femur, tibia, radius or ulna. In one embodiment, bone fixation device 50 is a humeral nail for implanting into the humerus.

Figure 7:
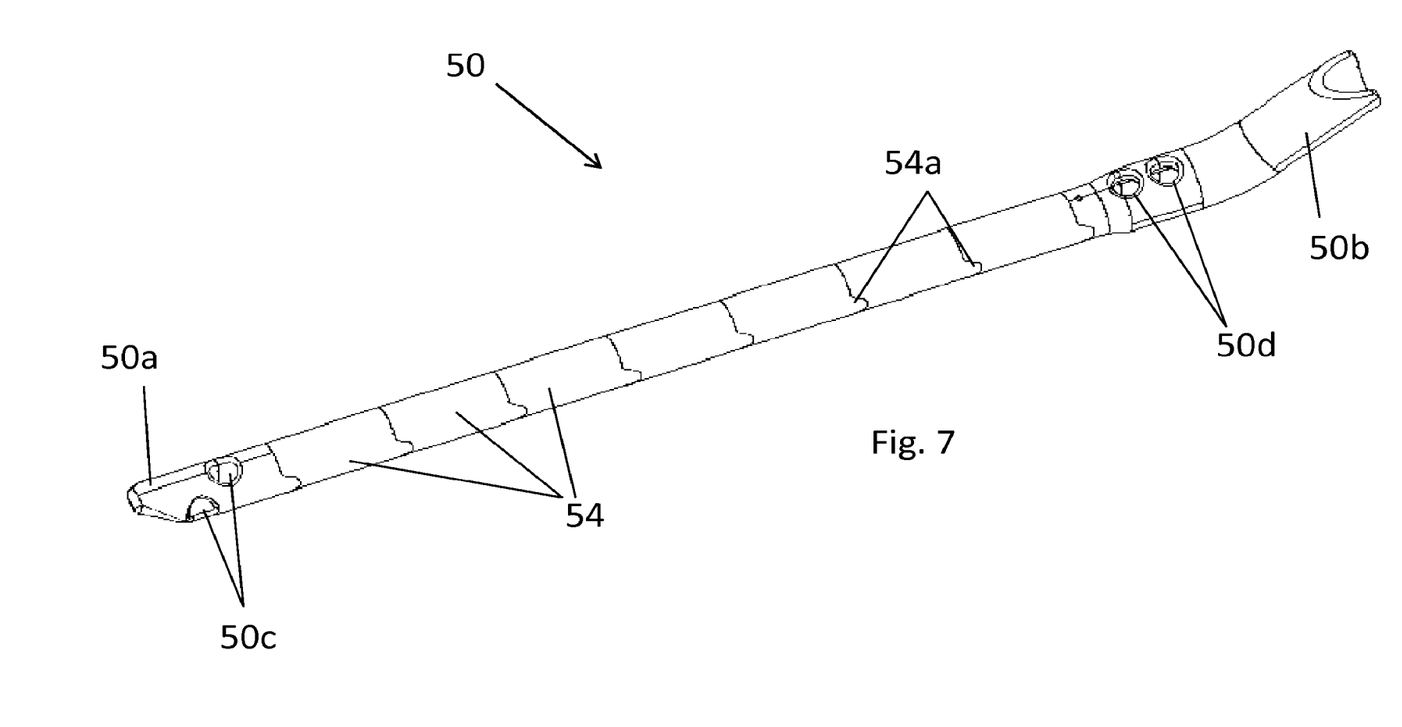
FIG. 7 is a perspective view of a bone fixation device in accordance with an exemplary embodiment of the present invention shown in a rigid configuration.
Figure 9A:
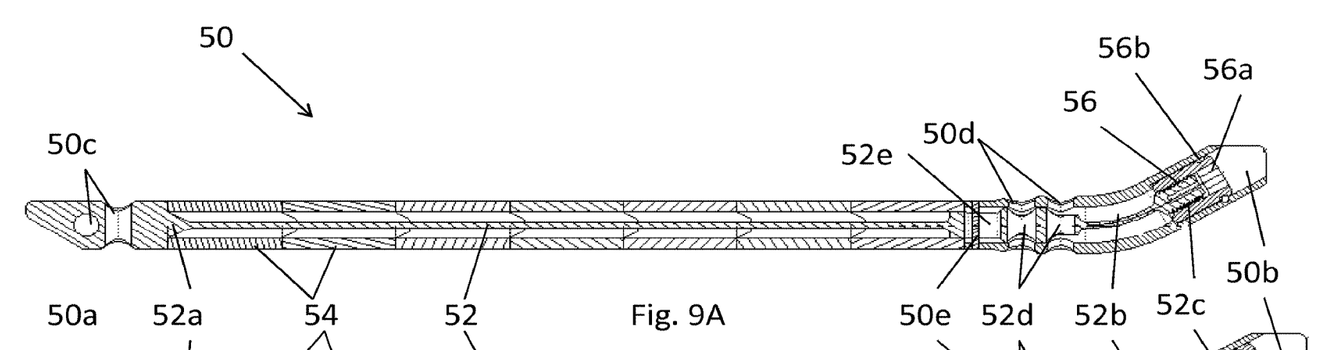
FIG. 9A is a cross sectional side view of the bone fixation device shown in FIG. 7 in a rigid configuration.

Referring to FIG. 7, bone fixation device 50 includes a plurality of rigid segments 54 that are moveable relative to one another in a flexible or implanting configuration (FIG. 9B) and are fixed relative to one another in a rigid or implanted configuration (FIG. 9A). In some embodiments, rigid means substantially unbending or stiff. In some embodiments, bone fixation device 50 and/or rigid segments 54 may bend slightly under extreme forces or due to material strength or machined tolerances. However, in some embodiments, bone fixation device is substantially stiffer in the implanted configuration than in the implanting configuration such that bone fixation device 50 can bend during implanting and be stiffened to provide support between bones or bone fragments once implanted.

In one embodiment, a distal end 50a is configured to be coupled to a first bone section and a proximal end 50b is configured to be coupled to a second bone section once implanted. In one embodiment, distal end 50a is generally pointed. In one embodiment, proximal end 50b is bent and the remainder of bone fixation device 50 is straight once implanted. In other embodiments, bone fixation device 50 is curved or any other shape in the rigid position to fit to a desired anatomy. In one embodiment, a substantial length of bone fixation device 50 is flexible in the implanting configuration. In other embodiments, only a portion of bone fixation device 50 is flexible in the implanting configuration. In one embodiment, the entire bone fixation device 50 is rigid in the implanted configuration. In other embodiments, at least a portion of bone fixation device 50 remains flexible in the implanted configuration. In one embodiment, bone fixation device 50 is comprised of biocompatible materials. In one embodiment, bone fixation device 50 is comprised of biocompatible metal.

In one embodiment, distal end 50a includes one or more apertures 50c configured to receive a fastener such as a pin or screw. In one embodiment, apertures 50c are perpendicular to one another. In one embodiment, proximal end 50b includes one or more apertures 50d. In one embodiment, apertures 50d are perpendicular to one another. In one embodiment, apertures 50c, 50d are approximately 2.4 mm to approximately 3.5 mm in diameter.

Figures 8A, 8B:
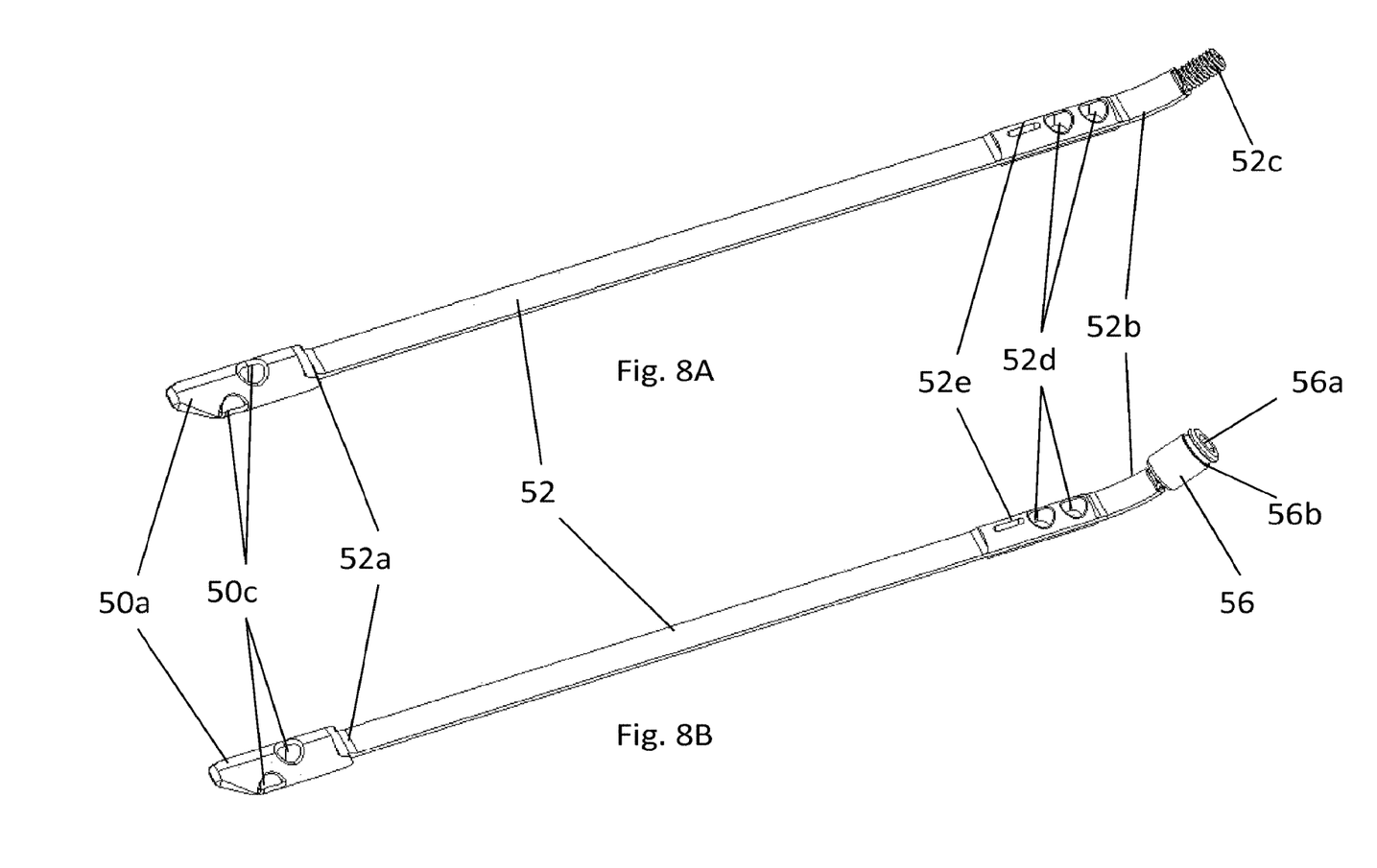
FIG. 8A is a perspective view of the bone fixation device shown in FIG. 7 with the plurality of segments removed.
FIG. 8B is a perspective view of the bone fixation device shown in FIG. 8A with a fixation sleeve attached to the proximal end.
Figure 9B:
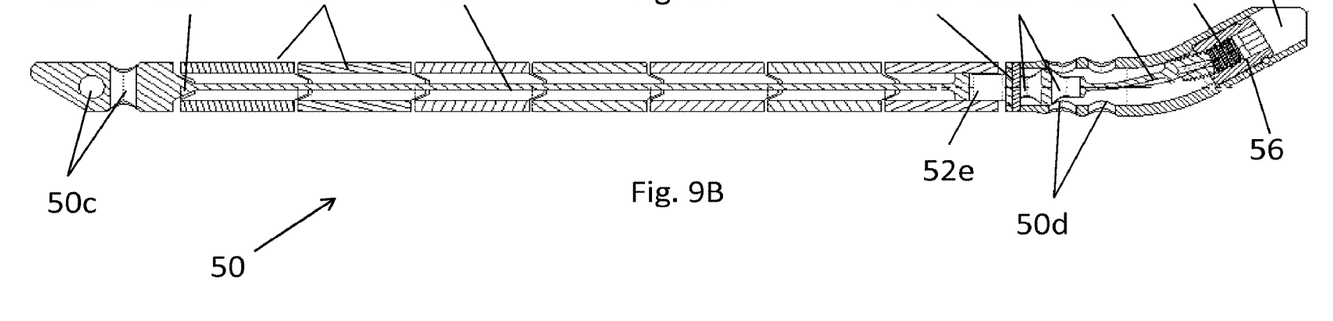
FIG. 9B is a cross sectional side view of the bone fixation device shown in FIG. 7 in a flexible configuration.

Referring to FIGS. 8A and 8B, which shows bone fixation device 50 with rigid segments 54 removed, bone fixation device includes a flexible body 52 secured to distal end 50a and movably attached to the proximal end 50b (see FIGS. 9A and 9B). In one embodiment, body 52 is flexible along a first plane and rigid along a second plane orthogonal to the second plane. In one embodiment, body 52 is rectangular cross section. In one embodiment, body 52 is wider than it is thick. In one embodiment, body 52 is machined out of a single block of material. In one embodiment, body 52 is comprised of multiple pieces joined together with pins, threads or other methods.

In one embodiment, body 52 is threadably attached to a radially rotatable, axially fixed sleeve 56 in the proximal end 50b. In one embodiment, sleeve 56 is cylindrical in shape and includes a groove 56b that mates with a corresponding projection or pins in proximal end 50b or vice versa. Sleeve 56 is configured to rotate relative to proximal end 50b and groove 56b and the corresponding projection from proximal end 50b prevents sleeve 56 from moving axially relative to proximal end 50b. In one embodiment, body 52 includes an external male screw thread 52c. In one embodiment, sleeve 56 includes an internal female screw thread 56b configured to mate with male screw thread 52c. In other embodiments, the threads 52c, 56b of body 52 and sleeve 56 are reversed. In one embodiment, a proximal end of sleeve 56 is configured to mate with a tool to rotate sleeve 56 relative to proximal end 50b. The proximal end of sleeve 56 may include any mating feature such as hex, slot, projection, Torx or Phillips shape for receiving the tool.

In one embodiment, body 52 includes at least one aperture 52d. In one embodiment, at least one aperture 52d of body 52 aligns with at least one aperture 50d of proximal end 50b in the rigid configuration. In one embodiment, body 52 includes a slot 52e configured to receive a projection or pin 50e (see FIGS. 9A and 9B). In one embodiment, pin 50e prevents proximal end from rotating relative to proximal end 50b.

Referring to FIGS. 9A and 9B, in one embodiment, rigid segments 54 are cannulated rigid segments that surround body 52. Rigid segments 54 may have any cross sectional shape such as rectangular, triangular or oval. In one embodiment, rigid segments 54 are cylinders. In one embodiment, there is a space between the inner surface of the rigid segments 54 and at least a portion of body 52. In one embodiment, any space between the inner surface of the rigid segments 54 and body 52 is filled with a material and/or includes a drug.

In one embodiment, rigid segments 54 have a contiguous outer surface. In one embodiment, rigid segments 54 include one or more apertures. In one embodiment, each rigid segment 54 includes at least one projection that mates with an indent of an adjacent segment. In one embodiment, each rigid segment includes an axially extending mating feature to prevent rigid segments 54 and proximal and distal ends 50a, 50b from rotating relative to one another in the rigid position.

In one embodiment, body 52 has a first length measured between distal and proximal ends 50a, 50b in the flexible configuration and a second length measured between distal and proximal ends 50a, 50b in the rigid configuration, the first length being greater than the second length. In one embodiment, rigid segments 54 are spaced in a flexible configuration to allow body 52 to flex. In one embodiment, rotating sleeve 56 draws body 52 axially relative to proximal end 50b causing distal end 50a to be closer to proximal end 50b and each of the rigid segments 54 to collapse and abut one another to form a rigid device.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

I claim:

1. A bone screw for drawing first and second bone fragments together, comprising:
   a shaft having a distal section and a proximal section, the distal section having a first external male screw thread and a minor diameter, the proximal section having a second external male screw thread, a major diameter of the distal section being larger than a major diameter of the proximal section; and
   a sleeve having an open proximal end and an open distal end and an internal female screw thread configured to mate with the second external male screw thread, a distal portion of the sleeve being tapered and having an outer diameter that tapers from a first outer diameter that is larger than the major diameter of the distal section of the shaft to a second outer diameter that is smaller than the major diameter of the distal section of the shaft,
   wherein an outer surface of the tapered distal portion of the sleeve from the first outer diameter to the second outer diameter is void of threads, the tapered distal portion of the sleeve comprising two or more axially extending slots extending through the outer surface of the tapered distal portion and proximally from the distal end of the sleeve between two or more flexible phalanges which include the internal female screw thread,
   wherein the sleeve is configured to slide over the second external male screw thread along a first portion of the proximal section of the shaft in a distal direction without rotating the sleeve relative to the shaft, and engage with and screw over the second external male screw thread for at least a complete revolution along a second portion of the proximal section of the shaft in the distal direction by rotating the sleeve relative to the shaft.

2. The bone screw of claim 1, wherein a pitch of the first external male screw thread is larger than a pitch of the second external male screw thread.

3. The bone screw of claim 1, wherein the proximal section of the shaft is a wire.

4. The bone screw of claim 1, wherein the sleeve includes two or more radially extending projections.

5. The bone screw of claim 1, wherein the major diameter of the distal section of the shaft is approximately 1.3 mm.

6. The bone screw of claim 1, wherein the proximal section of the shaft includes a smooth, non-threaded section proximate the distal section of the shaft.

7. The bone screw of claim 6, wherein a portion of the proximal section of the shaft extends proximally from the sleeve in a compressed position.

8. The bone screw of claim 1, wherein the distal portion of the sleeve is frustoconical in shape.

9. The bone screw of claim 1, wherein the outer surface of the tapered distal portion of the sleeve is smooth and configured to contact a surface of the first bone fragment when the shaft is engaged with the second bone fragment and can subsequently be drawn into a hole created by the shaft.

10. The bone screw of claim 1, wherein a proximal portion of the sleeve does not contain threads.

* * * * *